United States Patent [19]

Narisada et al.

[11] 4,226,864

[45] Oct. 7, 1980

[54] 7-SUBSTITUTED AMINOACETAMIDO OXADETHIACEPHALOSPORINS

[75] Inventors: Masayuki Narisada, Ibaraki; Teruji Tsuji, Takatsuki; Mitsuru Yoshioka, Toyonaka; Matsumura Hiromu, Ashiya; Yoshio Hamashima, Kyoto; Sadao Hayashi, Ashiya; Wataru Nagata, Nishinomiya, all of Japan

[73] Assignee: Shionogi & Co., Ltd., Osaka, Japan

[21] Appl. No.: 826,818

[22] Filed: Aug. 22, 1977

[30] Foreign Application Priority Data

Sep. 1, 1976 [JP] Japan ................... 51-105117

[51] Int. Cl.³ .................. A61K 31/535; C07D 265/04; C07D 413/02
[52] U.S. Cl. .................. 424/248.5; 424/248.51; 544/90; 542/419
[58] Field of Search .................. 544/90, 92, 27; 542/419; 424/248.5, 248.51

[56] References Cited

U.S. PATENT DOCUMENTS

| | | | |
|---|---|---|---|
| 3,996,218 | 12/1976 | Breuer et al. | 544/27 |
| 4,013,653 | 3/1977 | Wolfe | 544/90 |
| 4,015,000 | 3/1977 | Kocsis et al. | 260/239.1 X |
| 4,032,521 | 6/1977 | Christenen et al. | 544/21 X |
| 4,087,424 | 5/1978 | Saikawa et al. | 544/385 |
| 4,103,008 | 7/1978 | Toshiyasu et al. | 544/385 X |
| 4,110,327 | 8/1978 | Saikawa et al. | 544/385 |

FOREIGN PATENT DOCUMENTS 133593 12/1974 Japan ........................ 544/90

OTHER PUBLICATIONS

Firestone et al., J. Med. Chem., vol. 20, pp. 551 to 556 (4-77).
Lednicer et al., The Organic Chemistry of Drug Synthesis, pp. 408 to 415, 417 to 422 (p. 416 missing), John Wiley and Sons, NY (1977).
Cama et al., J. Am. Chem. Soc., vol. 96, pp. 7582-7584 (1974).
Kim et al., Tetrahedron Letters No. 5, pp. 409-412 (1978).
Chemical Abstracts, vol. 81, Abst. No. 37560f (1974) (Abst. of Ger. Offen. 2,355,209, apparent German equivalent of Japanese Patent 133,593 above).

*Primary Examiner*—John D. Randolph
*Attorney, Agent, or Firm*—Wenderoth, Lind & Ponack

[57] ABSTRACT

Antibacterial 7-substituted aminoacetamido oxadethiacephalosporins of the formula:

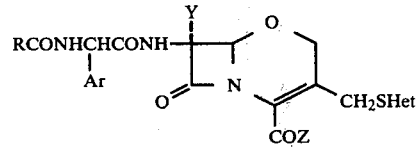

[wherein R is substituted amino, substituted phenyl, or 5- or 6-membered hetero ring; Ar is aryl; Y is hydrogen or methoxy; Het is 5- or 6-membered aromatic hetero ring; and Z is hydroxy or carboxy protecting group] preparable e.g. by acylation of 7α-methoxy-7β-amino-3-heterocyclic thiomethyl-3-cephem-4-carboxylic acid derivatives, are highly active against gram-positive and gram-negative bacteria, especially those resistant to other cephalosporins and penicillins.

16 Claims, No Drawings

7-SUBSTITUTED AMINOACETAMIDO OXADETHIACEPHALOSPORINS

This invention relates to oxadethia-cephalosporins, more specifically 7-substituted aminoacetamido oxadethia-cephalosporins, to esters thereof and to pharmaceutically acceptable salts thereof. Further, it relates to processes for their preparation.

The oxadethia-cephalosporins, the esters and the pharmaceutically acceptable salts are novel and useful medicament exhibiting excellent anti-bacterial activity.

Certain oxadethia-cephalosporins have been known. Japanese published application (not examined) No. 133,595/1974 discloses oxadethia-cephalosporins, but the compounds disclosed therein are different from the oxadethia-cephalosporins of this invention in the substituent at 7 position and in activity against resistant strains of bacteria.

According to this invention there is provided a compound of the formula:

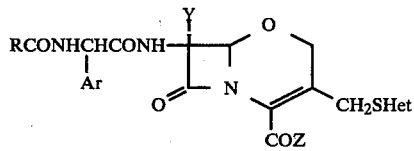

wherein
R is

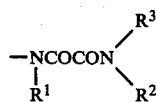

wherein $R^1$, $R^2$ and $R^3$ are independently hydrogen or lower alkyl, or $R^1$ and $R^2$, when taken together, are lower alkylene;

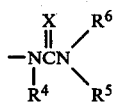

wherein X is imino, oxygen or sulfur, $R^4$, $R^5$ and $R^6$ are independently hydrogen or lower alkyl, $R^4$ and $R^5$, when taken together, are lower alkylene, lower alkenylene, o-phenylene or azo, $R^4$, $R^5$ and $R^6$, when taken together, are

(wherein $R^7$ is hydrogen or lower alkyl) or $R^6$ may be mesyl when $R^4$ and $R^5$ are taken together;

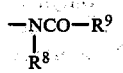

wherein $R^8$ is hydrogen or lower alkyl and $R^9$ is aralkyl, aralkenyl or aryl; substituted phenyl;

or 5- or 6-membered hetero ring containing 1 or 2 hetero atoms selected from nitrogen and sulfur which may have one or more substituents and/or a condensed ring;
Ar is aryl,
Y is hydrogen or methoxy,
Het is 5- or 6-membered aromatic hetero ring containing 1 to 4 hetero atoms selected from nitrogen, oxygen and sulfur, and Z is hydroxy or carboxy protecting group.

The following definitions are given for various terms used throughout this specification. The term "lower alkyl" refers to both straight and branched aliphatic radicals of one to five carbon atoms including, for example, methyl, ethyl, propyl, isopropyl, butyl. The term "lower alkylene" refers to both straight and branched alkylenes of one to five carbon atoms including, for example, methylene, ethylene, propylene, trimethylene. The term "lower alkenylene" refers to both straight and branched alkenylenes of 1 to 5 carbon atoms including, for example, vinylene, propenylene, pentenylene. The term "aryl" refers to both single and condensed aromatic rings which may contain one or more hetero atoms including, for example, phenyl, furyl, thienyl, pyrrolyl, imidazolyl, pyridyl, naphthyl, quinolyl, benzimidazolyl. The aromatic ring may be substituted with lower alkyl, lower alkoxy, hydroxy, organic or inorganic acyloxy group (e.g. acetyloxy or carbamoyloxy), halogen and the like. "Aralkyl" includes alkyls of one to five carbon atoms defined above substituted with the aryl noted above. The alkyl residue may have one or more substituents such as amino, carboxy and the like. The term "aralkenyl" refers to lower alkenyls of one to five carbon atoms substituted with aryl as exemplified in the term "aryl" including, for example, cinnamyl, 2-furylvinyl, and 3-thienylallyl.

Illustrative of the substituents in compound [I] are as follows:
When R is

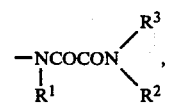

preferable examples are —NHCOCONH$_2$, —NHCOCON(CH$_3$)$_2$, —NCH$_3$COCONH$_2$, —NHCOCON(C$_2$H$_5$)$_2$, 4-methyl-2,3-dioxopiperazin-1-yl, and 4-ethyl-2,3-dioxopiperazin-1-yl. Of these, the more preferred are —NHCOCON(CH$_3$)$_2$, and 4-ethyl-2,3-dioxopiperazin-1-yl, and the most preferred is 4-ethyl-2,3-dioxopiperazin-1-yl.

When R is

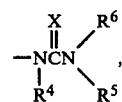

preferable examples are

—NHC(NH)NH$_2$, —NHC(NH)NHCH$_3$, —NHCONH$_2$, —NCH$_3$CONHCH$_3$, —NHCSNHCH$_3$, —NCH$_3$CSNH$_2$,

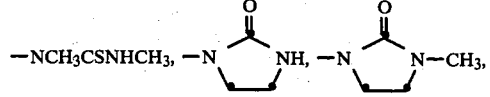

-continued

[Structures: -N(C=O)N-SO₂CH₃, -N(C=O)NH (unsaturated), benzimidazolone-type -N(C=O)NH fused to benzene]

[Structures: -N(COCH₃)-N=N-N-CH₃ (tetrazole acetyl), and -N(COCH₃)-N(CH₃)-N=N-N (tetrazole)]

among which —NCH₃CONHCH₃, —NCH₃CSNHCH₃,

[Structure: -N(C=O)NH imidazolone]

[Structures: -N(C=O)N-SO₂CH₃, and -N(COCH₃)-N=N-N-CH₃]

When R is $$-\underset{R^8}{N}CO-R^9,$$

preferable examples are —NCH₃COCH(NH₂)Ph (Ph means phenyl thoughout this specification), —NCH₃COCH(COOH)Ph, —NCH₃COCH=CHPh, —NCH₃COCH=CH—(2-thienyl), and —NCH₃CO—(2-furyl), and the most preferred is N-methyl-N-cinnamoylamino.

When R is a substituted phenyl, preferred substituents are lower alkyl, lower alkoxy, hydroxy and acyloxy. It is preferred that R is phenyl substituted with one to three hydroxys or acetyloxys.

When R is a 5- or 6-membered hetero ring containing one or two hetero atoms selected from nitrogen and sulfur which may have one or more substituents and/or a condensed ring, preferable examples are as follows:

[Structures: 4H-thiopyran-4-one, quinolin-4(1H)-one, 1-methylquinolin-4(1H)-one, indol-type, indol-type]

-continued

[Structures: various 1,8-naphthyridin-4(1H)-one derivatives with OCH₃, CH₃, SCH₃, pyrrolidinyl, piperazinyl substituents]

The symbol "Ar" means aryl group as noted above. Preferable aryls are phenyl and substituted phenyls (e.g. p-hydroxyphenyl, p-carbamoyloxyphenyl or p-acetoxyphenyl).

The symbol "Het" means 5- or 6-membered aromatic hetero ring containing one to four hetero atoms selected from nitrogen, oxygen and sulfur atoms which may be substituted with lower alkyl. Preferable examples are furyl, thienyl,

[Structures: tetrazolyl (NH), tetrazolyl (N-CH₃), triazolyl (NH), triazolyl (N-C₂H₅), thiadiazolyl, thiazolyl-CH₃, thiazolyl-C₂H₅, thiadiazole, and thiadiazole-CH₃]

the more preferable being 1-methyl-1H-tetrazol-5-yl.

This invention also includes pharmaceutically acceptable salts and esters, namely the compounds [I] having a protected carboxy at the 4-position, i.e. COZ in the formula [I] being protected carboxy.

The salt includes organic and inorganic salts, for example, sodium, potassium, magnesium, calcium, triethylamine, dicyclohexylamine, morpholine, and N-methylmorpholine salts and the like.

The ester includes t-butyl, acyloxymethyl, phthalidyl, diphenylmethyl, trityl, benzyl, p-nitrobenzyl, p-methoxybenzyl, 2,2,2-trichloroethyl, 2-haloethyl and phenacyl esters, other easily removable aliphatic esters, aromatic esters (e.g. phenyl or indanyl ester) and the like, which are conventional carboxy protecting groups generally used in the chemistry of penicillins and cephalosporins.

Preferable compounds [I] include a compound of the following formula or its pharmaceutically acceptable salts:

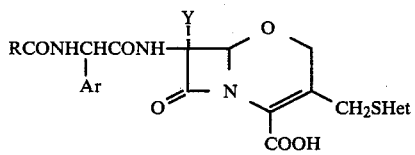
[Ia]

(wherein
R is 1,3-dimethylureido, 1,3-dimethylthioureido, 3-methanesulfonyl-2-oxoimidazolidin-1-yl, N-methyl-N-cinnamoylamino, 3,4-diacetoxyphenyl, 4-oxothiopyran-3-yl, 8-ethyl-3-methoxy-5-oxo-5,8-dihydropyrido[2,3-c]pyridazin-6-yl, 4-methyl-2,3-dioxopiperazin-1-yl, 4-ethyl-2,3-dioxopiperazin-1-yl, or 4-propyl-2,3-dioxopiperazin-1-yl;

Ar is phenyl, hydroxyphenyl, carbamoyloxyphenyl, hydroxyfluorophenyl, or acetoxyphenyl;

Y is hydrogen or methoxy; and

Het is 1-methyltetrazol-5-yl, 1,3,4-thiadiazol-5-yl, 2-methyl-1,3,4-thiadiazol-5-yl, or 1,2,3-thiazol-4-yl).

More preferable of the compounds [I] have the following definitions in the formula [Ia] above:

(1) Y is hydrogen, Ar is phenyl or p-hydroxyphenyl, Het is 1-methyltetrazol-5-yl, and R is 1,3-dimethylureido;

(2) Y is hydrogen, Ar is phenyl or p-hydroxyphenyl, Het is 1-methyltetrazol-5-yl, and R is 1,3-dimethylthioureido;

(3) Y is hydrogen, Ar is phenyl or p-hydroxyphenyl, Het is 1-methyltetrazol-5-yl, and R is 3-methanesulfonyl-2-oxoimidazolidin-1-yl;

(4) Y is hydrogen, Ar is phenyl, Het is 1-methyltetrazol-5-yl, and R is N-methyl-N-cinnamoylamino;

(5) Y is hydrogen, Ar is phenyl, Het is 1-methyltetrazol-5-yl, and R is 3,4-diacetoxyphenyl;

(6) Y is hydrogen, Ar is phenyl, Het is 1-methyltetrazol-5-yl, and R is 8-ethyl-3-methoxy-5-oxo-5,8-dihydropyrido[2,3-c]pyridazin-6-yl;

(7) Y is methoxy, Ar is phenyl, Het is 1-methyltetrazol-5-yl, and R is 4-propyl-2,3-dioxopiperazin-1-yl;

(8) Y is methoxy, Ar is p-hydroxyphenyl, Het is 1-methyltetrazol-5-yl, and R is 4-propyl-2,3-dioxopiperazin-1-yl; or (9) Y is methoxy, Ar is p-hydroxyphenyl, Het is 2-methyl-1,3,4-thiadiazol-5-yl, and R is 4-propyl-2,3-dioxopiperazin-1-yl.

Other representatives of the compounds [I] are those shown by the following formula or their pharmaceutically acceptable salts:

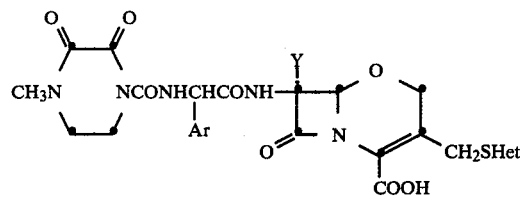

wherein the substituents are defined as follows (1) Y is hydrogen, Ar is phenyl, and Het is 1-methyltetrazol-5-yl;

(2) Y is hydrogen, Ar is phenyl, and Het is 2-methyl-1,3,4-thiadiazol-5-yl;

(3) Y is hydrogen, Ar is phenyl, and Het is 1,3,4-thiadiazol-5-yl;

(4) Y is hydrogen, Ar is p-hydroxyphenyl, and Het is 1-methyltetrazol-5-yl;

(5) Y is hydrogen, Ar is p-hydroxyphenyl, and Het is 2-methyl-1,3,4-thiadiazol-5-yl;

(6) Y is hydrogen, Ar is p-hydroxyphenyl, and Het is 1,3,4-thiadiazol-5-yl;

(7) Y is hydrogen, Ar is p-carbamoyloxyphenyl, and Het is 1-methyltetrazol-5-yl;

(8) Y is hydrogen, Ar is p-carbamoyloxyphenyl, and Het is 2-methyl-1,3,4-thiadiazol-5-yl;

(9) Y is hydrogen, Ar is p-carbamoyloxyphenyl, and Het is 1,3,4-thiadiazol-5-yl;

(10) Y is hydrogen, Ar is p-acetoxyphenyl, and Het is 1-methyltetrazol-5-yl;

(11) Y is methoxy, Ar is phenyl, and Het is 1-methyltetrazol-5-yl;

(12) Y is methoxy, Ar is phenyl, and Het is 2-methyl-1,3,4-thiadiazol-5-yl;

(13) Y is methoxy, Ar is phenyl, and Het is 1,3,4-thiadiazol-5-yl;

(14) Y is methoxy, Ar is p-hydroxyphenyl, and Het is 1-methyltetrazol-5-yl;

(15) Y is methoxy, Ar is p-hydroxyphenyl, and Het is 2-methyl-1,3,4-thiadiazol-5-yl;

(16) Y is methoxy, Ar is p-hydroxyphenyl, and Het is 1,3,4-thiadiazol-5-yl;

(17) Y is methoxy, Ar is p-carbamoyloxyphenyl, and Het is 1-methyltetrazol-5-yl;

(18) Y is methoxy, Ar is p-carbamoyloxyphenyl, and Het is 2-methyl-1,3,4-thiadiazol-5-yl;

(19) Y is methoxy, Ar is p-carbamoyloxyphenyl, and Het is 1,3,4-thiadiazol-5-yl; and

(20) Y is methoxy, Ar is 4-hydroxy-2-fluorophenyl, and Het is 1,2,3-triazol-4-yl.

Further representatives of the compounds [I] are those shown by the following formula or their pharmaceutically acceptable salts:

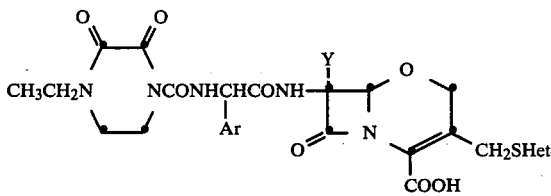

wherein the substituents are as follows (1) Y is hydrogen, Ar is phenyl, and Het is 1-methyltetrazol-5-yl;

(2) Y is hydrogen, Ar is phenyl, and Het is 2-methyl-1,3,4-thiadiazol-5-yl;
(3) Y is hydrogen, Ar is phenyl, and Het is 1,3,4-thiadiazol-5-yl;
(4) Y is hydrogen, Ar is p-hydroxyphenyl, and Het is 1-methyltetrazol-5-yl;
(5) Y is hydrogen, Ar is p-hydroxyphenyl, 2nd Het is 2-methyl-1,3,4-thiadiazol-5-yl;
(6) Y is hydrogen, Ar is p-hydroxyphenyl, and Het is 1,3,4-thiadiazol-5-yl;
(7) Y is hydrogen, Ar is p-carbamoyloxyphenyl, and Het is 1-methyltetrazol-5-yl;
(8) Y is hydrogen, Ar is p-carbamoyloxyphenyl, and Het is 2-methyl-1,3,4-thiadiazol-5-yl;
(9) Y is hydrogen, Ar is p-carbamoyloxyphenyl, and Het is 1,3,4-thiadiazol-5-yl;
(10) Y is hydrogen, Ar is p-acetoxyphenyl, and Het is 1-methyltetrazol-5-yl;
(11) Y is methoxy, Ar is phenyl, and Het is 1-methyltetrazol-5-yl;
(12) Y is methoxy, Ar is phenyl, and Het is 2-methyl-1,3,4-thiadiazol-5-yl;
(13) Y is methoxy, Ar is phenyl, and Het is 1,3,4-thiadiazol-5-yl;
(14) Y is methoxy, Ar is p-hydroxyphenyl, and Het is 1-methyltetrazol-5-yl;
(15) Y is methoxy, Ar is p-hydroxyphenyl, and Het is 2-methyl-1,3,4-thiadiazol-5-yl;
(16) Y is methoxy, Ar is p-hydroxyphenyl, and Het is 1,3,4-thiadiazol-5-yl;
(17) Y is methoxy, Ar is p-carbamoyloxyphenyl, and Het is 1-methyltetrazol-5-yl;
(18) Y is methoxy, Ar is p-carbamoyloxyphenyl, and Het is 2-methyl-1,3,4-thiadiazol-5-yl;
(19) Y is methoxy, Ar is p-carbamoyloxyphenyl, and Het is 1,3,4-thiadiazol-5-yl; and
(20) Y is methoxy, Ar is 4-hydroxy-2-fluorophenyl; and Het is 1,2,3-triazol-4-yl.

Most preferable pharmaceutically acceptable salts of these compounds [Ia] are sodium and potassium salts.

The compounds [Ia] are especially useful antibacterials very active against gram negative bacteria, even against some pseudomonal strains.

Pseudomonal bacteria is effectively dissolved under high dose of 4-lower alkyl-2,3-dioxopiperazinyl derivatives among the compounds [I], although the activity of the drug is reversible at lower concentration after formation of long filament of bacteria. The compounds are excreted through urinary tract and in hepatic juice.

The process for preparing the compounds [I] is explained below although almost of them are within the possession of those skilled in the art as standardized method of synthesis in β-lactam chemistry. The following description briefly explains some of the procedures, but they are not an exhaustive list of the method for the preparation.

(1) Acylation of 7-amino on the cephem ring.

The compound [II] having a free amino group at the 7-position is acylated to give a desired compound [I]

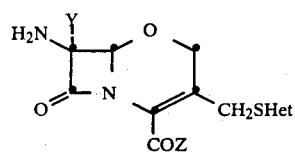

[II]

[wherein Het, Y and Z are as defined above] by treating it with an acylating agent of the formula:

$$RCONHCHCOW \quad \text{[III]}$$
$$\quad\quad\quad\ \ |$$
$$\quad\quad\quad\ \ Ar$$

[wherein R and Ar are as defined above and W is reactive functional group] to acylate the 7-amino group. The 7-amino group may be activated before the reaction into the form of isocyano, isocyanato, 1-haloalkylideneamino, 1-alkoxyalkylideneamino, silylamino, enamine and the like. The compound [III] is, for example, free acid, acid halogenide, acid anhydride, active ester, active amide, ketene and the like having a desired acyl residue. The acylation may be effected in the presence of a base (e.g. triethylamine, pyridine or sodium hydrogencarbonate), molecular sieve, carbodiimide (e.g. dicyclohexylcarbodiimide), epoxide (e.g. propylene oxide or butylene oxide) and enzyme, if desired. In the process, acid chloride method, acid anhydride method, carbodiimide method and active ester method can be employed.

(2) Acylation of α-amino group of 7-glycylamino group.

Desired compounds [I] can be obtained by acylating α-amino group of a 7-glycylamino group of a compound [IV]. The process can be effected as follows:

A compound of the formula:

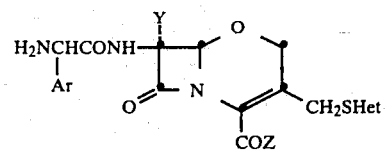

[IV]

[wherein Ar, Y, Z and Het are as defined above] is acylated with an acylating agent of the formula:

RCOW [V]

[wherein R and W are as defined above] at the α-amino group of the 7-glycylamino group. The α-amino group can be activated before the acylation in the same manner as described in (1).

(3) Introduction of thio-hetero ring residue to the 3-methyl group.

Desired compounds [I] can be obtained by introducing thio-hetero ring residue to a compound [I] lacking the thio-hetero ring residue at 3 position. The process is effected by reacting a compound of the formula:

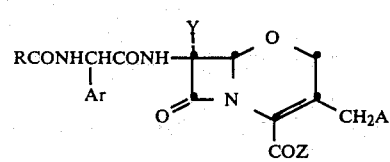

[VI]

[wherein R, Ar, Y and Z are as defined above and A is leaving group] with a compound of the formula:

HetSH or the metal salt [VII]

[wherein Het is as defined above].

(4) Introduction of a protecting group to 4-carboxy group.

Desired compounds [I] can be obtained by introducing a protecting group to 4-carboxy group of a compound [I] which has a free carboxy group at 4 position. Desired esters can be prepared by esterifying a compound [I] in a conventional manner using the compounds [I] with a free carboxy group at 4 position. Desired salts can be obtained from the compounds [I] having a free carboxy group at 4 position by usual methods. The starting compound [I] is dissolved in an alcohol (e.g. methanol, ethanol, or propanol), ketone (e.g. acetone or methyl ethyl ketone), ether (e.g. ether, tetrahydrofuran or dioxane), ester (e.g. ethyl acetate) solvent and the like. To the solution of the free acid is added a solution of a suitable salt of lower alkanoate (e.g. sodium acetate, potassium propionate, potassium 2-ethyl hexanoate or sodium lactate) in a suitable solvent described above. The objective salt can be obtained as a precipitate or crystals from the mixture by adding ethyl acetate.

(5) Removal of a protecting group from 4-carboxy group.

Desired compounds [I] can be prepared by removal of a protecting group of 4-carboxy group from a compound [I] having a protected carboxy group at 4 position. The removal may be effected by hydrolysis, reduction, solvolysis, photochemical reaction and other suitable conventional methods to remove the protecting group.

(6) Introduction of 7α-methoxy group.

Introduction of 7α-methoxy group to a compound [I] gives a desired methoxy compound [I] when the starting compound [I] has a hydrogen as Y in the formula [I].

The methoxy group can be introduced in a usual manner, for example, by the reaction with lithium methoxide and t-butyl hypohalogenite in methanol.

(7) Other usual methods to prepare penicillins and cephalosporins.

Other useful methods used in this field can be employed to prepare desired compounds [I].

The oxadethia-cephalosporins of this invention are useful and highly active antibacterials against gram negative strains and strains resistant to other cephalosporins and penicillins.

The antibacterial activity of some typical compounds [I] dissolved in an aqueous sodium hydrogencarbonate solution are shown in Table I.

Table I

| Tested Bacteria | Compound | Minimal Inhibitory Concentration (mcg/ml) | | |
|---|---|---|---|---|
| | | A | B | C |
| Staphylococcus aureus C-14 | | 1.6 | 3.1 | 1.6 |
| Escherichia coli NIHJ JC-2 | | 0.2 | 0.01 | 0.1 |
| Escherichia coli 73 | | 0.4 | 12.5 | 25 |
| Klebsiella pneumoniae | | 0.01 | 0.01 | 0.05 |
| Klebsiella sp. 363 | | 0.1 | 12.5 | 100 |
| Proteus mirabilis PR-4 | | 0.4 | 0.4 | 1.6 |
| Proteus vulgaris CN-329 | | 0.2 | 0.2 | 0.8 |
| Enterobacter cloacae 233 | | 0.8 | 0.1 | 0.8 |
| Serratia marcescens 13880 | | 0.8 | 0.05 | 0.8 |
| Pseudomonas aeruginosa 25619 | | 3.1 | 0.8 | 0.8 |
| Pseudomonas aeruginosa Denken | | 12.5 | 6.3 | 6.3 |

Table I-continued

| Tested Bacteria | Compound | Minimal Inhibitory Concentration (mcg/ml) | | |
|---|---|---|---|---|
| | | A | B | C |
| Pseudomonas aeruginosa 24 | | 25 | 3.1 | 6.3 |

Notes:
Test compounds (sodium salt)
A = 7α-Methoxy-7β-[D-α-phenyl-N-(4-ethyl-2,3-dioxo-1-piperazinylcarbonyl)-glycylamino]-3-(1-methyl-1H-tetrazol-5-ylthiomethyl)-1-oxadethia-3-cephem-4-carboxylic acid
B = 7-[D-α-(p-hydroxyphenyl)-N-(4-ethyl-2,3-dioxo-1-piperazinylcarbonyl)-glycylamino]-3-(1-methyl-1H-tetrazol-5-ylthiomethyl)-1-oxadethia-3-cephem-4-carboxylic acid
C = 7-[D-α-(p-hydroxyphenyl)-N-(4-ethyl-2,3-dioxo-1-piperazinylcarbonyl)-glycylamino]-3-(1-methyl-1H-tetrazol-5-ylthiomethyl)-3-cephem-4-carboxylic acid (reference compound)

The compounds [I] thus have stronger antibacterial activity, against gram positive bacteria (e.g. Staphylococcus aureus Streptococcus pyogenes, Bacillus subtilis, Bacillus cereus, Diplococcus pneumoniae, Corynebacterium diphtheriae) and especially against gram negative bacteria (e.g. Escherichia coli, Klebsiella pneumoniae, Proteus mirabilis, Proteus vulgaris, Proteus rettgeri, Proteus morganii, Enterobacter cloacae, Shigella sonnei, Salmonella paratyphi, Salmonella typhi, Serratia marsescens), and some are active even against Pseudomonas aeruginosa. The other compounds of this invention show antibacterial activity similar to the test compounds.

The compounds [I] including some esters and pharmaceutically acceptable salts thereof are useful in the prevention or treatment of various human and veterinary infections caused by bacteria sensitive to the compounds [I]. Such infections include pneumonia, bronchitis, pneumonitis, empyema, nasopharyngitis, tonsillitis, rhinitis, dermatitis, pustulosis, ulceration, abses, wound and soft tissue infections, ear infections, osteomyelitis, septicemia, gastroenteritis, enteritis, urinary tract infections, and pyelonephritis when caused by bacteria sensitive to Compound (I).

The compounds [I] can be administered solely or as a mixture. Furthermore, the compounds can be administed in combination with pharmaceutically acceptable carriers, diluents, adjuvants and other suitable medicines, if desired.

The carrier is determined in accordance with the chemical properties of the compound [I] to be used and the purpose and route of administration. Examples of solid carriers for internal and external use are lactose, sucrose, starch, dextrin, sodium hydrogencarbonate, licorice powder, talc, kaoline, bentonite, calcium carbonate, paraffin and the like. As gel or liquid carrier, there are exemplified gelatine, water, ethanol, i-propanol, chloroform, glycerol and the like. Freon (Trade Mark) is available for use with the compound [I] in the form of aerosols.

Practical examples of suitable forms of pharmaceutical preparation of compounds [I] are tablets, capsules, pills, granules, powders and the like for oral administration and injectable solutions, ointments, aerosols, suppositories and the like for parenteral administration.

The pharmaceutical compositions of this invention may contain 0.01% to 99% by weight of compound [I] as an active ingredient. The compounds [I] are generally administered intravenously to human beings or other animals at a daily dose of about 250 mg to 5 g, though the amount can be changed according to the purpose, condition of patient, sensitivity of infecting bacteria, and route and interval of administration.

Further, Compounds (I) are also useful intermediates for preparing useful antibiotics within or beyond the scope of Compounds (I).

The following examples are given solely for the purpose of illustration and are not to be construed as limiting this invention.

EXAMPLE 1

(1) D-α-(4-Ethyl-2,3-dioxo-1-piperizinylcarbonylamino)phenylacetic acid (128 mg) is suspended in dry benzene (4 ml), and oxalyl chloride (34 μl) and dimethylformamide (3 μl) are added thereto. The mixture is stirred for 2 hours at room temperature, and evaporated to dryness under reduced pressure. Benzene is added thereto and the mixture is evaporated to dryness to give D-α-(4-ethyl-2,3-dioxo-1-piperazinylcarbonylamino)phenylacetyl chloride.

Separately, diphenylmethyl 7α-methoxy-7β-amino-3-(1-methyl-1H-tetrazol-5-ylthiomethyl)-1-oxadethia-3-cephem-4-carboxylate (101.7 mg) is dissolved in dichloromethane (3 ml) and cooled to 0° C. A solution of the above D-α-(4-ethyl-2,3-dioxo-1-piperazinylcarbonylamino)phenylacetyl chloride in dichloromethane (2 ml) is added to the mixture, and after 5 minutes pyridine (16 μl) is added thereto. The mixture is stirred for 2.5 hours at 0° C. and diluted with ethyl acetate, extracted with sodium hydrogencarbonate solution and water. The extract is dried over sodium sulfate, and evaporated to dryness under reduced pressure. The residue is subjected to silica gel column chromatography. From 2% acetic acid-ethyl acetate eluates diphenylmethyl 7α-methoxy-7β-[D-α-phenyl-N-(4-ethyl-2,3-dioxo-1-piperazinylcarbonyl)-glycylamino]-3-(1-methyl-1H-tetrazol-5-ylthiomethyl)-1-oxadethia-3-cephem-4-carboxylate (30.2 mg) is obtained as a colorless foam.

IR $\nu_{max}^{CHCl_3}$: 3410, 3280, 1790, 1710, 1685 cm$^{-1}$.

NMR $\delta^{CDCl_3}$: 1.17t(7 Hz)3H, ca 3.4 4H, 3.50s3H, 3.85s3H, ca 3.9 2H, 4.27s2H, 4.52s2H, 5.07s1H, 5.64d(7 Hz)1H, 9.88d(7 Hz)1H.

(2) A solution of the product obtained above (25.1 mg) in dichloromethane is cooled to 0° C. Anisole (0.05 ml) and trifluoroacetic acid (0.1 ml) are added to the solution, which is stirred for 30 minutes at 0° C. and evaporated to dryness under reduced pressure. The residue is triturated with ether to give 7α-methoxy-7β-[D-α-phenyl-N-(4-ethyl-2,3-dioxo-1-piperazinylcarbonyl)-glycylamino]-3-(1-methyl-1H-tetrazol-5-ylthiomethyl)-1-oxadethia-3-cephem-4-carboxylic acid (13.8 mg) as a colorless powder. Yield: 69.2%.

mp. 152°-156° C. IR $\nu_{max}^{KBr}$: 1785, 1713, 1680 cm$^{-1}$.

EXAMPLE 2

(1) D-α-(p-Hydroxyphenyl)-N-(1,3-dimethylureidocarbonyl)-glycine (59 mg) is dissolved in a mixture of dimethylformamide (0.5 ml) and dichloromethane (0.5 ml) in nitrogen atmosphere. N-methylmorpholine (26 μl) and ethyl chlorocarbonate (20 μl) are added thereto at −5° C. and the mixture is stirred for 30 minutes at the same temperature. To this mixture is added diphenylmethyl 7-amino-3-(1-methyl-1H-tetrazol-5-ylthiomethyl)-1-oxadethia-3-cephem-4-carboxylate (100 mg) in dichloromethane (2 ml) at −30° C., and the resulting mixture is stirred for 1.5 hours at the same temperature. The mixture is diluted with a proper amount of dichloromethane, washed two times with an ice-cooled sodium hydrogencarbonate solution, two times with 1 N hydrochloric acid, and three times with water, dried over magnesium sulfate. The solvent is evaporated under reduced pressure to yield a colorless oil. The oil is treated with a small amount of benzene-ethyl acetate (9:1) to give diphenylmethyl 7-[D-α-(p-hydroxyphenyl)-N-(1,3-dimethylureidocarbonyl)-glycylamino]-3-(1-methyl-1H-tetrazol-5-ylthiomethyl)-1-oxadethia-3-cephem-4-carboxylate (75 mg) as colorless crystals. Yield: 48.4%.

mp. 218°-220° C. (d)

IR: $\nu_{max}^{Nujol}$ 3340, 3230, 1801, 1732, 1685, 1660, 1640 cm$^{-1}$.

NMR $\delta^{d6\text{-}DMSO}$: 2.70d(4 Hz)3H, 3.13s3H, 3.95s3H, 4.32brs2H, 4.68brs2H, 5.23d(4 Hz)1H, 5.33d(7 Hz)1H, 5.73dd (4;10 Hz)1H, 6.7-7.8 ml6H, 9.02d(10 Hz)1H, 9.37s1H, 9.82d(7 Hz)1H.

Besides, D-α-(p-hydroxyphenyl)-N-(dimetylureidocarbonyl)-glycine can be prepared by reacting D-[−]-α-(p-hydroxyphenyl)-glycine with trimethylsilyldiethylamine followed by the reaction of the resulting D-α-(p-trimethylsilyloxyphenyl-N-trimethylsilyl)-glycine trimethylsilyl with dimethylureidocarbonyl chloride.

mp. 218°-220° C. (d)

(1') To a suspension of diphenylmethyl 7-amino-3-(1-methyl-1H-tetrazol-5-ylthiomethyl)-1-oxadethia-3-cephem-4-carboxylate (800 mg) in acetonitrile (10 ml), O,N-bis-(trimethylsilyl)-acetamide (1.7 ml) is added and completely dissolved. The solution is evaporated under reduced pressure to remove excess acetonitrile and to give diphenylmethyl 7-(N,N-bistrimethylsilylamino)-3-(1-methyl-1H-tetrazol-5-ylthiomethyl)-1-oxadethia-3-cephem-4-carboxylate.

Besides, D-α-(p-hydroxyphenyl)-N-(1,3-dimethylureidocarbonyl)glycine (470 mg) and N-hydroxybenztriazole (226 mg) are dissolved in tetrahydrofuran (5 ml) in nitrogen atmosphere, and a solution of dicyclohexylcarbodiimide (412 mg) in tetrahydrofuran (2 ml) is added thereto with ice-cooling. The mixture is stirred for 1 hour and 45 minutes at room temperature and the resultant precipitate is filtered off. The above prepared solution of diphenylmethyl 7-(N,N-bistrimethylsilylamino)-3-(1-methyl-1H-tetrazol-5-ylthiomethyl)-1-oxadethia-3-cephem-4-carboxylate in dichloromethane (25 ml) is added to the filtrate with ice-cooling, and stirred for 3.5 hour at room temperature. The reaction mixture is washed three times with water, dried over magnesium sulfate, and the solvent is evaporated under reduced pressure. The residue is subjected to silica gel (containing 10% water) column chromatography. The eluates of ethyl acetate are collected and evaporated to dryness to give diphenylmethyl 7-[D-α-(p-hydroxyphenyl)-N-(1,3-dimethylureidocarbonyl)-glycylamino]-3-(1-methyl-1H-tetrazol-5-ylthiomethyl)-1-oxadethia-3-cephem-4-carboxylate (850 mg) as colorless crystals. Yield: 68.5%.

(2) The product of the above (1) or (1') is treated in the same manner as in Example 1(2) to give 7-[D-α-(p-hydroxyphenyl)-N-(1,3-dimethylureidocarbonyl)-glycylamino]-3-(1-methyl-1H-tetrazol-5-ylthiomethyl)-1-oxadethia-3-cephem-4-carboxylic acid.

mp. 160°-180° C.

IR $\nu_{max}^{KBr}$: 3400, 2940, 1784, 1682, 1632 cm$^{-1}$.

$[\alpha]_D^{23}$: −71.8±2.1 (c=0.522 in 1% NaHCO$_3$)

EXAMPLE 3

To a solution of D-N-(3,4-diacetoxybenzoyl)phenylglycine (116 mg) and diphenylmethyl 7-amino-3-(1-methyl-1H-tetrazol-5-ylthiomethyl)-1-oxadethia-3-cephem-4-carboxylate (100 mg) in dichloromethane (4 ml) is added 1-ethoxycarbonyl-2-ethoxy-3,4-dihydroquinoline (77 mg) and stirred for 3 hours at room temperature. The reaction mixture is extracted with ethyl acetate and water, and the ethyl acetate layer is successively washed with dilute hydrochloric acid, a sodium hydrogencarbonate solution, water, and a sodium chloride solution. The mixture is dried and the solvent is evaporated. The residue is subjected to silica gel (containing 10% water) column chromatography, and the fractions, eluted with benzene-ethyl acetate (1:1), are collected and evaporated to dryness to give diphenylmethyl 7-[D-N$^\alpha$-(3,4-diacetoxybenzoyl)phenylglycylamino]-3-(1-methyl-1H-tetrazol-5-ylthiomethyl)-1-oxadethia-3-cephem-4-carboxylate (107 mg).

Yield: 61.8%.

NMR $\delta^{CDCl_3}$: 2.23s6H, 3.73s3H, 4.23brs2H, 4.38brs2H, 4.90d(4 Hz)1H, 5.65dd(4;9 Hz)1H, 5.97d(7 Hz)1H, 6.97s1H, 7.0–7.9 m.

(2) The product obtained in (1) hereinabove is treated in the same manner as in Example 1(2) to give 7-[D-N$^\alpha$-(3,4-diacetooxybenzoyl)phenylglycylamino]-3-(1-methyl-1H-tetrazol-5-ylthiomethyl)-1-oxadethia-3-cephem-4-carboxylic acid.

IR $\nu_{max}^{CHCl_3}$: 1780, 1700, 1660 cm$^{-1}$.
Rf=0.78 (ethyl acetate:acetic acid:water=3:1:1);
0.58 (chloroform:methanol=1:1);
0.24 (chloroform:methanol=3:1).

EXAMPLES 4–9

The following compounds are prepared in accordance with the same procedures as described in Examples 1–3.

Table II

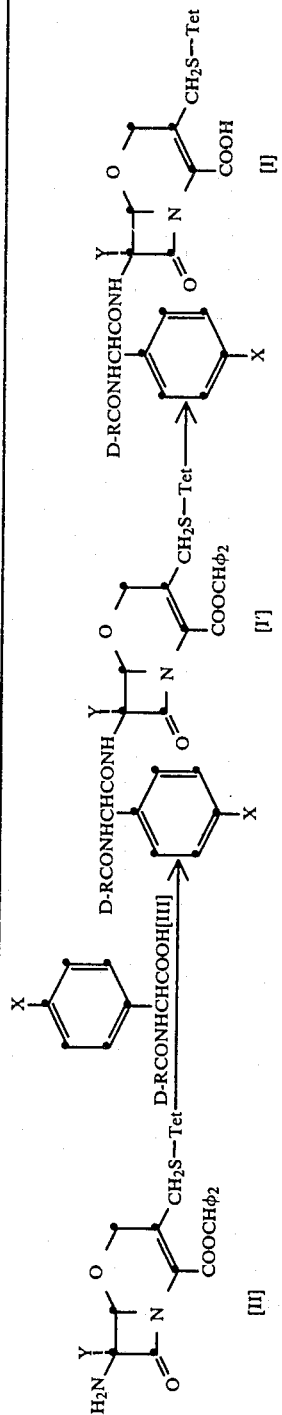

| Example | Compound II Y | Compound III R | X | Compound [I'] | Compound I |
|---|---|---|---|---|---|
| 4 | H | (4-methyl-thiopyranone ring) | H | IR $\nu_{max}^{CHCl_3}$: 3410, 1802, 1707, 1668, 1605 1512 cm$^{-1}$<br>NMR $\delta^{CDCl_3}$: 3.82s3H, 4.28brs2H, 4.52brs 2H, 5.02d(4Hz)1H, 5.75dd (9.4Hz)1H, 5.93d(8Hz)1H, 6.95s1H, 7.10–7.93m18H, 9.17d(4Hz)1H, 11.02d(8Hz)1H. | mp. 185°–190° C.<br>IR $\nu_{max}^{KBr}$:3410, 1779, 1665, 1603 1522 cm$^{-1}$ |
| 5 | H | (CH$_3$SO$_2$-imidazolidinone) | H | IR $\nu_{max}^{CHCl_3}$: 3415, 1803, 1743, 1697, 1390, 1365, 1171 cm$^{-1}$<br>NMR $\delta^{CDCl_3}$: 3.18s3H, 3.57–3.87m7H, 4.12brs 2H, 4.47brs2H, 4.87d(4Hz)1H, 5.40–5.80m2H, 6.85s1H, 7.00–7.67m16H, 7.12d(8Hz)1H. | mp. 178°–185° C.<br>IR $\nu_{max}^{KBr}$: 3400, 1789, 1740, 1690, 1394, 1358, 1169 cm$^{-1}$ |
| 6 | H | (CH$_3$SO$_2$-imidazolidinone) | OH | IR $\nu_{max}^{CHCl_3}$: 3315, 3320, 1803, 1743, 1717, 1697, 1513, 1391, 1365, 1170 cm$^{-1}$<br>NMR $\delta^{CDCl_3}$: 3.27s3H, 3.67–3.83m7H, 4.25brs 2H, 4.62brs2H, 5.10d(4Hz)1H, 5.57–5.90m2H, 6.67–7.80m15H, 8.15d(10Hz)1H, 8.83d(8Hz)1H. | mp. 204°–211° C.<br>IR $\nu_{max}^{KBr}$: 3390, 1772, 1739, 1683, 1614, 1355, 1168 cm$^{-1}$ |
| 7 | H | CH$_3$–N(N)–<br>PhCH=CHCO<br>(mp.124°–126° C.) | H | D-Racemate<br>IR $\nu_{max}^{CHCl_3}$: 3680, 3430, 3250, 1802, 1697, 1616, 1499 cm$^{-1}$<br>NMR $\delta^{CDCl_3}$: 3.38s3H,3.75s3H, 4.25s2H,4.55s2H,4.98d(4Hz)1H, 5.65d(7Hz)1H,5.72dd(10.4Hz)1H,6.93d(15Hz)1H, 6.97s1H,7.10d(10Hz)1H,7.40s20H,7.85s(15Hz)1H, 10.37d(7Hz)1H.<br>(L-racemate)<br>IR $\nu_{max}^{CHCl_3}$: 3695,3435,3275,1800,1693,1613,1496 cm$^{-1}$<br>NMR $\delta^{CDCl_3}$: 3.35s3H,3.83s3H,4.27s2H,4.62s2H,5.10d(4Hz)1H, 5.5–5.8m2H,6.87d(15Hz)1H,6.90s1H,6.8–7.6m21H,7.80d (15Hz)1H, 10.42d(7Hz)1H. | D-racemate<br>mp.155°–158° C.<br>IR $\nu_{max}^{Nujol}$:3295,1788,1779,1724,1676, 1664,1634,1620,1604,1525 cm$^{-1}$<br>UV $\lambda_{max}^{EtOH}$:284nm($\epsilon$ = 28,760)<br>(L-racemate)<br>mp.137°–141° C.<br>Rf = 0.2(ethylacetate:acetic acid:water = 16:1:1) |

Table II-continued $$\text{H}_2\text{N}\underset{\text{[II]}}{\overset{Y}{\diagdown}}\text{...CH}_2\text{S—Tet, COOCH}\phi_2 \xrightarrow{\text{D-RCONHCHCOOH[III]}} \text{D-RCONHCHCONH}\underset{\text{[I']}}{\overset{Y}{\diagdown}}\text{...CH}_2\text{S—Tet, COOCH}\phi_2 \rightarrow \text{D-RCONHCHCONH}\underset{\text{[I]}}{\overset{Y}{\diagdown}}\text{...CH}_2\text{S—Tet, COOH}$$

| | Compound II | Compound III | | Compound [I'] | Compound I |
|---|---|---|---|---|---|
| Example | Y | R | X | | |
| 8 | H | CH₃NHCS—N(CH₃)— <br> IR: $\nu_{max}^{CHCl_3}$ 1721 cm$^{-1}$ | H | D-racemate <br> Rf = 0.44 (benzene:ethyl acetate = 4:1) <br> IR $\nu_{max}^{CHCl_3}$:3450,1800,1715,1695,1665 cm$^{-1}$ <br> NMR $\delta$ CDCl₃ : 3.10d(4.5Hz)3H,3.80s3H,3.95s3H,4.25s2H,4.55s2H 5.00d(4Hz)1H,5.37d(5Hz)1H,5.65dd(9,4Hz)1H,6.48d (9Hz)1H,6.83d(5Hz)1H,6.97s1H,7.2–7.7m11H. <br><br> (epimer) <br> Rf = 0.35 <br> IR $\nu_{max}^{CHCl_3}$:3420,1800,1715,1692,1667 cm$^{-1}$ <br> NMR $\delta$ CDCl₃:3.10d(4.5Hz)3H,3.78s3H,3.85s3H,4.28s2H,4.63d (6Hz)2H,5.10d(4Hz)1H,5.40d(5Hz)1H,5.67dd(8,4Hz) 1H,6.77d(5Hz)1H,6.98s1H,7.0–7.7m11H. | IR $\nu_{max}^{KBr}$:3400,1789,1670,1515,1500 cm$^{-1}$ |
| 9 | H | (structure with CH₃O, N=N, N—C₂H₅, C=O ring) <br> (mp.225°–227° C.) | H | IR $\nu_{max}^{CHCl_3}$: 3430,3240,1799,1702,1640,1592,1518 cm$^{-1}$ <br> NMR $\delta$ CDCl₃:1.50t(7Hz)3H,3.77s3H,4.07–4.70m9H,5.0d(4Hz)1H, 5.33–6.3m2H,6.97s1H,7.0–7.78m15H,7.85s1H,9.02s 1H,10.60(8Hz)1H. | IR $\nu_{max}^{CHCl_3}$:3411,3245,1792,1694,1659, 1594 cm$^{-1}$ |

EXAMPLE 10

(1) Potassium salt of D-α-(p-hydroxyphenyl)-N-(1-methoxycarbonyl-3-propenyl)glycine (154 mg) is suspended in acetone (3.0 ml) and N-methylmorpholine (3 mg) is added thereto. To the mixture is added ethyl chlorocarbonate (59 mg), with stirring at −25° C. to −20° C., and the stirring is continued for an additional 1 hour at the same temperature. After the addition of a solution of diphenylmethyl 7-amino-3-(1-methyl-1H-tetrazol-5-ylthiomethyl)-1-oxadethia-3-cephem-4-carboxylate (200 mg) in dichloromethane (2.0 ml) over a period of 2 minutes, the mixture is gradually warmed to 10° C. through 2 hours. Benzene-ethyl acetate (1:1, 10 ml) and water (10 ml) are added to the reaction mixture, and the solvent is evaporated under reduced pressure. The residue is subjected to silica gel (containing 10% water) column chromatography. The fractions, eluted with benzene-ethyl acetate (1:1), are collected and evaporated to give diphenylmethyl 7-[D-α-(p-hydroxyphenyl)-N-(1-methoxycarbonyl-2-propenyl)-glycylamino]-3-(1-methyl-1H-tetrazol-5-ylthiomethyl)-1-oxadethia-3-cephem-4-carboxylate (210 mg). Yield: 69%.

NMR $\delta^{CDCl_3}$: 1.90s3H, 3.64s3H, 3.75s3H, 4.24brs2H, 4.60brs2H, 4.95d(4 Hz)1H, 5.05d(7 Hz)1H, 5.60dd(4;9 Hz)1H, 6.75A$_2$B$_2$(9 Hz)2H, 6.80s1H, 6.90s1H, 9.10d(7 Hz)1H, 7.2–7.6 ml3H.

(2) The product obtained in (1) hereinabove, is treated in the same manner as in Example 1(2) to give 7-[D-α-(p-hydroxyphenyl)glycylamino]-3-(1-methyl-1H-tetrazol-5-ylthiomethyl)-1-oxadethia-3-cephem-4-carboxylic acid trifluoroacetate.

IR $\nu_{max}^{KBr}$: 3400–2400, 1790, 1695 (sh), 1678 cm$^{-1}$.

EXAMPLE 11

D-α-(p-Hydroxyphenyl)-N-(t-butyloxycarbonyl)glycine (140 mg) and N-hydroxytriazole (78 mg) are dissolved in tetrahydrofuran (1 ml). The solution is stirred with ice-cooling and dicyclohexylcarbodiimide (124 mg) is added thereto. The mixture is stirred for 1 hour at the same temperature and an additional 1 hour at room temperature. Then the resultant precipitate is filtered off to give a solution of an active ester.

Separately, O,N-bis(trimethylsilyl)acetamide (0.3 ml) is added to a suspension of diphenylmethyl 7-amino-3-(1-methyl-1H-tetrazol-5-ylthiomethyl)-1-oxadethia-3-cephem-4-carboxylate (240 mg) in acetonitrile (2 ml) and stirred for 20 minutes at room temperature. The mixture is evaporated to dryness under reduced pressure (5 mmHg) at 50° C. The residue is dissolved in tetrahydrofuran (1.5 ml) and stirred with ice-cooling. The solution of active ester, prepared hereinbefore, is added thereto and the mixture is stirred for 10 minutes at 0° C. and then for 2 hours at room temperature. The reaction mixture is poured into ethyl acetate, washed with water, dried over magnesium sulfate, and the solvent is evaporated. The residue is recrystallized with chloroform to give diphenylmethyl 7-[D-α-(p-hydroxyphenyl)-N-(t-butyloxycarbonyl)glycylamino]-3-(1-methyl-1H-tetrazol-5-ylthiomethyl)-1-oxadethia-3-cephem-4-carboxylate (235 mg).

Yield: 65%.

m.p. 173°–175° C. (dec.).

IR $\nu_{max}^{Nujol}$: 3330, 1790, 1722, 1682 cm$^{-1}$.

NMR $\delta^{CD_3OD}$: 1.43s9H, 3.87s3H, 4.02s2H, 4.60s2H, 5.07d(4 Hz) 1H, 5.20s1H, 5.68d(4 Hz)1H, 6.80d(9 Hz)2H, 6.88s1H, 7.2–7.7 ml3H.

(2) The product (200 mg) obtained hereinabove, is added to a mixture of anisole (0.30 ml) and trifluoroacetic acid (0.5 ml) with ice-cooling, and stirred for 1 hour with ice-cooling. Benzene is added thereto, and the solvent is evaporated under reduced pressure. The residue is washed with ether to give 7-[D-α-(p-hydroxyphenyl)glycylamino]-3-(1-methyl-1H-tetrazol-5-ylthiomethyl)-1-oxadethia-3-cephem-4-carboxylic acid trifluoroacetate (140 mg). Yield: 89%.

EXAMPLE 12

(1) A solution of 7-(D-α-p-hydroxyphenylglycylamino)-3-(1-methyl-1H-tetrazol-5-ylthiomethyl)-1-oxadethia-3-cephem-4-carboxylic acid trifluoroacetate (75 mg) in tetrahydrofuran (2.0 ml) is vigorously stirred with ice-cooling, and a solution of 4-ethyl-2,3-dioxo-1-piperazinylcarbonyl chloride (100 mg) in tetrahydrofuran (0.5 ml) and an 5% aqueous sodium hydrogencarbonate solution (2.0 ml) are added at the same time over a period of 5 minutes thereto followed by stirring for 30 minutes at 0° C. Tetrahydrofuran is evaporated in nitrogen atmosphere and water is added to the mixture. The mixture is washed with ethyl acetate and neutralized with dilute hydrochloric acid to deposite an oil. The water layer is evaporated to dryness under reduced pressure. The residue is extracted with methanol and the extract is evaporated to remove the solvent. This residue and the deposited oil hereinbefore are subjected to silica gel (containing 10% water) column chromatography. The fractions of ethyl acetate-acetic acid (5:1) are collected and evaporated to give pure and hygroscopic 7-[D-α-(p-hydroxyphenyl)-N-(4-ethyl-2,3-dioxo-1-piperazinylcarbonyl)glycylamino]-3-(1-methyl-1H-tetrazol-5-ylthiomethyl)-1-oxadethia-3-cephem-4-carboxylic acid (11 mg) as a powder.

Elementary analysis for C$_{25}$H$_{26}$N$_8$O$_9$S 2H$_2$O

Calcd. (%): C, 46.17; H, 4.66; N, 17.23; S, 4.92

Found (%): C, 46.30; H, 4.55; N, 17.36; S, 4.80

IR $\nu_{max}^{KBr}$: 3350, 1790, 1715, 1675 cm$^{-1}$.

NMR $\delta^{CDCl_3-CD_3OD(1:1)}$: 1.15t(7 Hz)3H, 3.50–4.70 mlOH, 3.97s3H, 5.02d(4 Hz)1H, 5.45s1H, 5.53d(4 Hz)1H, 6.93d(9 Hz)2H, 7.32d(9 Hz)2H.

(1') Propylene oxide (0.50 ml) and bis(trimethylsilyl)-acetamide (0.25 ml) are added to a suspension of 7-(D-α-p-hydroxyphenylglycylamino)-3-(1-methyl-1H-tetrazol-5-ylthiomethyl)-1-oxadethia-3-cephem-4-carboxylic acid trifluoroacetate (130 mg) in acetonitrile (2 ml) with ice-cooling and the mixture is stirred for 10 minutes followed by addition of 4-ethyl-2,3-dioxo-1-piperazinylcarbonyl chloride (46 mg). The mixture is stirred for 1 hour at 0° C. and an additional 30 minutes at room temperature, followed by addition of 5% aqueous sodium hydrogencarbonate solution and ethyl acetate. The aqueous layer is washed with ethyl acetate, adjusted to pH 2 with dilute hydrochloric acid, and a precipitate is filtered. The filtrate is subjected to column chromatography using silica gel (containing 10% water). The fractions eluted with acetone-acetic acid (10:1), are collected and evaporated to give 7-[D-α-(p-hydroxyphenyl)-N-(4-ethyl-2,3-dioxo-1-piperazinylcarbonyl)glycylamino]-3-(1-methyl-1H-tetrazol-5-ylthiomethyl)-1-oxadethia-3-cephem-4-carboxylic acid (95 mg) as a powder. Yield: 68%.

EXAMPLE 13

(1) Trichloroacetylisocyanate (0.30 ml) is added to a solution of diphenylmethyl 7-[D-α-(p-hydroxyphenyl)-N-(4-ethyl-2,3-dioxo-1-piperazinylcarbonyl)- glycylamino]-3-(1-methyl-1H-tetrazol-5-ylthiomethyl)-1-oxadethia-3-cephem-4-carboxylate (60 mg) in dichloromethane (2 ml) with ice-cooling, and stirred for 2 hours. The reaction mixture is poured into ice-water and extracted with chloroform. The extract is washed with water, dried, and evaporated to remove the solvent. The residue is dissolved in chloroform and then subjected to silica gel (containing 10% water) chromatography. The fractions, of chloroform-methanol (30:1), are collected and evaporated to give diphenylmethyl 7-[D-α-(p-carbamoyloxyphenyl)-N-(4-ethyl-2,3-dioxo-1-piperazinylcarbonyl)glycylamino]-3-(1-methyl-1H-tetrazol-5-ylthiomethyl)-1-oxadethia-3-cephem-4-carboxylate (50 mg) as a powder. Yield: 80%.

IR $\nu_{max}^{CHCl_3}$: 3500, 3400, 3270, 1780, 1740, 1705, 1680 cm$^{-1}$.

NMR $\delta^{CDCl_3:CD_3OD\ (5:1)}$: 1.20t(7 Hz)3H, 3.3–4.7 mlOH, 3.86s3H, 5.08d(4 Hz)1H, 5.65dd (4;7 Hz)1H, 5.68brs1H, 5.95s1H, 7.20d(8 Hz)2H.

(2) The product obtained in (1) hereinabove, is treated in the same manner as in Example 1(2) to give 7-[D-α-(p-carbamoyloxyphenyl)-N-(4-ethyl-2,3-dioxo-1-piperazinylcarbonyl)glycylamino]-3-(1-methyl-1H-tetrazol-5-ylthiomethyl)-1-oxadethia-3-cephem-4-carboxylic acid (33 mg) as a powder. Yield: 83%.

IR $\nu_{max}^{KBr}$: 3270, 1775, 1720(sh), 1700, 1655 cm$^{-1}$.

EXAMPLE 14

(1) Acetic anhydride (0.10 ml) and pyridine (0.05 ml) are added to a solution of diphenylmethyl 7-[D-α-(p-hydroxyphenyl)-N-(4-ethyl-2,3-dioxo-1-piperazinylcarbonyl)glycylamino]-3-(1-methyl-1H-tetrazol-5-ylthiomethyl)-1-oxadethia-3-cephem-4-carboxylate (70 mg) in dichloromethane (1 ml) with ice-cooling, and stirred for 2 hours. The reaction mixture is poured into water, stirred for 1 hour at room temperature, and extracted with chloroform. The extract is washed with water, dried, and the solvent is evaporated. The residue is washed with ether, and the resulting powder is subjected to chromatography using silica gel (containing 10% water). The elution with chloroform-methanol (30:1) gives diphenylmethyl 7-[D-α-(p-acetoxyphenyl)-N-(4-ethyl-2,3-dioxo-1-piperazinylcarbonyl)-glycylamino]-3-(1-methyl-1H-tetrazol-5-ylthiomethyl)-1-oxadethia-3-cephem-4-carboxylate (60 mg) as a powder. Yield: 82%.

IR $\nu_{max}^{CHCl_3}$: 3270(br), 1790, 1755(sh), 1712, 1685 cm$^{-1}$.

NMR $\delta^{CDCl_3}$: 1.20t(7 Hz)3H, 2.26s3H, 3.2–4.7 mlOH, 3.84s3H, 5.00d(4 Hz)1H, 5.70d(7 Hz)1H, 5.75dd(4;7 Hz)1H, 6.88s1H, 7.08d(9 Hz)2H, 10.01d(7 Hz)1H.

(2) The product obtained in (1) hereinabove, is treated in the same manner as in Example 1(2) to give 7-[D-α-(p-acetoxyphenyl)-N-(4-ethyl-2,3-dioxo-1-piperazinylcarbonyl)glycylamino]-3-(1-methyl-1H-tetrazol-5-ylthiomethyl)-1-oxadethia-3-cephem-4-carboxylic acid (43 mg) as a powder. Yield: 90%.

mp. 165°–170° C. (d)

IR $\nu_{max}^{KBr}$: 3270(br), 1785, 1750(sh), 1710, 1675 cm$^{-1}$.

EXAMPLE 15

(1) To a solution of diphenylmethyl 7-[D-α-(p-hydroxyphenyl)-N-(t-butyloxycarbonyl)glycylamino]-3-(1-methyl-1H-tetrazol-5-ylthiomethyl)-1-oxadethia-3-cephem-4-carboxylate (420 mg) in dry tetrahydrofuran (30 ml) are added t-butoxy chloride (85 ml) with stirrng at −78° C., and after 1 minute, 2 mM lithium methoxide in methanol (1.20 ml). The reaction mixture is kept for 10 minutes at the same temperature, followed by addition of acetic acid (10 ml) and stirring for 10 minutes. After addition of water (5.0 ml), ethyl acetate and water are added thereto at room temperature. The ethyl acetate layer is separated, washed with a dilute, aqueous sodium carbonate solution and water, dried over magnesium sulfate, and the solvent is evaporated. Chloroform is added to the residue, and the deposited crystals are filtered off. The filtrate is subjected to column chromatography using silica gel (containing 10% water), and elution with benzene-ethyl acetate (2:1) provides diphenylmethyl 7α-methoxy-7β-[D-α-(p-hydroxyphenyl)-N-(t-butyloxycarbonyl)glycylamino]-3-(1-methyl-1H-tetrazol-5-ylthiomethyl)-1-oxadethia-3-cephem-4-carboxylate (220 mg) as a powder.

Yield: 50%.

IR $\nu_{max}^{CHCl_3}$: 3410(br), 1790, 1708 cm$^{-1}$.

NMR $\delta^{CDCl_3}$: 1.40s9H, 3.50s3H, 3.68s3H, 4.18brs2H, 4.46brs 2H, 5.00s1H, 5.30 1H, 5.80 2H, 6.76d(9Hz)2H, 6.92s1H.

(2) The product obtained hereinabove is treated in the same manner as in Example 11(2) to give 7α-methoxy-7β-[D-α-(p-hydroxyphenyl)glycylamino]-3-(1-methyl-1H-tetrazol-5-ylthiomethyl)-1-oxadethia-3-cephem-4-carboxylic acid trifluoroacetate.

EXAMPLE 16

(1) To a suspention of 7α-methoxy-7β-[D-α-(p-hydroxyphenyl)-glycylamino]-3-(1-methyl-1H-tetrazol-5-ylthiomethyl)-1-oxadethia-3-cephem-4-carboxylic acid trifluoroacetate (160 mg), obtained in Example 15, in acetonitrile (2 ml) are added propylene oxide (0.50 ml) and O,N-bis(trimethylsilyl)acetamide (0.30 ml) with ice-cooling. The mixture is stirred for 20 minutes and 4-ethyl-2,3-dioxo-1-piperazinylcarbonyl chloride (70 mg) is added thereto a dilute aqueous sodium hydrogencarbonate solution and ethyl acetate are added thereto after stirring for 1 hour each at 0° C. and at room temperature. The dilute sodium hydrogencarbonate layer is separated, washed with ethyl acetate and neutralized with dilute hydrochloric acid. The precipitate is filtered and the filtrate is subjected to chromatography using silica gel (containing 10% water). The fractions, eluted with acetone-acetic acid (4:1), are collected and evaporated to give 7α-methoxy-7β-[D-α-(p-hydroxyphenyl)-N-(4-ethyl-2,3-dioxo-1-piperazinylcarbonyl)-glycylamino]-3-(1-methyl-1H-tetrazol-5-yl-thiomethyl)1-oxadethia-3-cephem-4-carboxylic acid (90 mg) as a powder. Yield: 52%.

mp. 182°–186° C. (d).

IR $\nu_{max}^{KBr}$: 3275 (br), 1775, 1708, 1670 cm$^{-1}$.

EXAMPLE 17

(1) The diphenylmethyl ester (50 mg) of the compound obtained in Example 16, is suspended in dichloro methane (2 ml) and stirred for 1.5 hours after addition of trichloroacetylisocyanate (0.50 ml) with ice-cooling. Water is added thereto and the mixture is extracted with chloroform. The extract is washed with water and the solvent is evaporated. The residue is subjected to column chromatography using silica gel (containing 10% water), followed by elution with chloroform-methanol (20:1) to give diphenylmethyl 7α-methoxy-7β-[D-α-(p-carbamoyloxyphenyl)-N-(4-ethyl-2,3-dioxo-1-piperazinylcarbonyl)glycylamino]-3-(1-methyl-1H-tetrazol-5-ylthiomethyl)-1-oxadethia-3-cephem-4-carboxylate (30 mg) as a powder.

IR $\nu_{max}^{CHCl_3}$: 3500, 3420, 3270, 1785, 1740(sh), 1715, 1690 cm$^{-1}$.

NMR $\delta$CDCl$_3$-CD$_3$OD (5:1): 1.20t(7 Hz)3H, 3.40–4.60ml OH, 3.60s3H, 3.85s3H, 5.10s1H, 5.60brs2H, 5.75brs1H, 6.95s1H, 7.12d(9Hz)2H, 9.75brs1H.

(2) The product obtained hereinabove, is treated in the same manner as in Example 1(2) to give 7α-methoxy-7β-[D-α-(p-carbamoyloxyphenyl)-N-(4-ethyl-2,3-dioxo-1-piperazinylcarbonyl)-glycylamino]-3-(1-methyl-1H-tetrazol-5-ylthiomethyl)-1-oxadethia-3-cephem-4-carboxylic acid (22 mg).

IR $\nu_{max}^{KBr}$: 3290(br), 1780, 1730(sh), 1700, 1670(sh) cm$^{-1}$.

EXAMPLE 18

(1) Diphenylmethyl 7-amino-3-(1-methyl-1H-tetrazol-5-ylthiomethyl)-1-oxadethia-3-cephem-4-carboxylate (248 mg) is dissolved in a mixture of tetrahydrofuran (8 ml) and acetone (4 ml). To the solution are added N-butoxycarbonyl-D-α-phenylglycyine (197 mg) and then 1-ethoxycarbonyl-2-ethoxy-3,4-dihydroquinoline (192 mg) in nitrogen atmosphere at room temperature, and the mixture is stirred for 2 hours at room temperature. Additionally, N-butoxycarbonyl-D-α-phenylglycine (66 mg) and 1-ethoxycarbonyl-2-ethoxy-3,4-dihydroquinoline (65 mg) are added thereto, and the mixture is stirred over night at room temperature. Ethyl acetate is added thereto, and the mixture is successively washed with 2N hydrochloric acid, water, a 5% aqueous sodium hydrogencarbonate solution and water. The organic layer is separated and dried over sodium sulfate. After evaporating the solvent, the residue is subjected to column chromatography using silica gel (containing 10% water). The elution with benzene-acetone (4:1), gives diphenylmethyl 7-[D-α-phenyl-N-(t-butoxycarbonyl)glycylamino]-3-(1-methyl-1H-tetrazol-5-ylthiomethyl)-1-oxadethia-3-cephem-4-carboxylate (309 mg).

IR $\nu_{max}^{CHCl_3}$: 3430, 1800, 1710, 1690 cm$^{-1}$.

NMR $\delta^{CDCl_3}$: 7.00s1H, 6.83d(9Hz)1H, 5.73dd(4;9Hz)1H, 5.63d(6Hz)1H, 5.26dd(6Hz)1H, 5.05d(4Hz)1H, 4.63brs2H, 4.30brs2H, 3.83s3H, 1.40s9H.

(2) The product obtained hereinabove is treated in the same manner as in Example 1(2) to give 7-(D-α-phenyl-glycylamino)-3-(1-methyl-1H-tetrazol-5-ylthiomethyl)-1-oxadethia-3-cephem-4-carboxylic acid trifluoroacetate (125 mg) as a colorless powder.

mp. 146°–154° C. (d)

IR $\nu_{max}^{Nujol}$: 1785, 1680 cm$^{-1}$.

NMR $\delta^{D_2O-DCl}$: 7.52s5H, 5.50d(4Hz)1H, 5.32s1H, 5.20d (4Hz)1H, 4.57brs2H, −4.1 2H, 4.05s3H.

EXAMPLE 19

The same operation as in Example 12(1) using 7-D-α-phenylglycylamino-3-(1-methyl-1H-tetrazol-5-ylthiomethyl)-1-oxadethia-3-cephem-4-carboxylic acid trifluoroacetate gives crystals of 7-[α-phenyl-N-(4-ethyl-2,3-dioxo-1-piperazinylcarbonyl)glycylamino]-3-(1-methyl-1H-tetrazol-5-ylthiomethyl)-1-oxadethia-3-cephem-4-carboxylic acid (54 mg). Yield: 66%.

mp. 169°–171° C.

IR $\nu_{max}^{KBr}$: 1780, 1705, 1670 cm$^{-1}$

EXAMPLE 20

The reaction of 7-(D-α-phenylglycylamino)-3-(1-methyl-1H-tetrazol-5-ylthiomethyl)-1-oxadethia-3-cephem-4-carboxylic acid trifluoroacetate (80 mg) with dimethylureidocarbonyl chloride (82 mg) is effected in the same manner as in Example 15(1) to give 7-[D-α-phenyl-N-(1,3-dimethylureidocarbonyl)glycylamino]-3-(1-methyl-1H-tetrazol-5-ylthiomethyl)-1-oxadethia-3-cephem-4-carboxylic acid (26 mg) as a colorless powder. Yield: 32.5% mp. 143°–148° C.

$[\alpha]_D^{22.5}$: −95.9°±6.3° (c=0.217: 1% aqueous sodium hydrogencarbonate)

IR $\nu_{max}^{KBr}$: 3400, 1787, 1682, 1637, 1512 cm$^{-1}$.

EXAMPLE 21

Propylene oxide (1.2 ml) and bis(trimethylsilyl)-acetamide (0.5 ml) are added to a suspension of 7-(D-α-p-hydroxyphenylglycylamino)-3-(1-methyl-1H-tetrazol-5-ylthiomethyl)-1-oxadethia-3-cephem-4-carboxylic acid trifluoroacetate (300 mg) in acetonitrile (5 ml) with ice-cooling, and stirred for 10 minutes at 0° C. 4-Methyl-2,3-dioxo-1-piperazinylcarbonyl chloride (150 mg) is added thereto, and the mixture is stirred for 1 hour at the same temperature and additional 1 hour at room temperature. The mixture is treated in the same manner as in Example 12(1') to give 7-[D-α-(p-hydroxyphenyl)-N-(4-methyl-2,3-dioxo-1-piperazinylcarbonyl)-glycylamino]-3-(1-methyl-1H-tetrazol-5-ylthiomethyl)-1-oxadethia-3-cephem-4-carboxylic acid (180 mg). Yield: 56%.

IR $\nu_{max}^{KBr}$: 3280, 1780, 1700, 1680 cm$^{-1}$.

The diphenylmethyl ester of the above compound shows the following physical constants.

IR $\nu_{max}^{CDCl_3}$: 3290, 1793, 1715, 1692 cm$^{-1}$

NMR $\delta$CDCl$_3$:CD$_3$OD (5:1): 2.97s3H, 3.50–4.60m8H, 3.75s3H, 4.90d(4Hz)1H, 5.45d(6Hz)1H, 5.50d-d(4Hz;9Hz)1H, 6.69d (7Hz)2H, 6.75s1H, 9.77d(6Hz)1H.

EXAMPLE 22

(1) Diphenylmethyl 7-[D-α-(p-hydroxyphenyl)-N-(4-methyl-2,3-dioxo-1-piperazinylcarbonyl)glycylamino]-3-(1-methyl-1H-tetrazol-5-ylthiomethyl)-1-oxadethia-3-cephem-4-carboxylate (100 mg), obtained in Example 21, is reacted with trichloroacetylisocyanate (0.4 ml) in the same manner as in Example 13(1), to give diphenylmethyl 7-[D-α-(p-carbamoyloxyphenyl)-N-(4-methyl-2,3-dioxo-1-piperazinylcarbonyl)-glycylamino]-3-(1-methyl-1H-tetrazol-5-ylthiomethyl)-1-oxadethia-3-cephem-4-carboxylate (85 mg) as a foam. Yield: 80%.

IR $\nu_{max}^{CHCl_3}$: 3280, 1788, 1740, 1715, 1685 cm$^{-1}$.

NMR $\delta$CDCl$_3$: CD$_3$OD(5:1): 3.03s3H, 3.40–4.60m8H, 3.80s3H, 4.98d(4Hz)1H, 5.50–5.80brs3H, 6.85s1H, 7.04d(9Hz)2H, 9.90d (6Hz)1H.

(2) The compound obtained in (1) hereinbefore, is treated in the same manner as in Example 1(2) to give 7-[D-α-(p-carbamoyloxyphenyl)-N-(4-methyl-2,3-dioxo-1-piperazinylcarbonyl)glycylamino]-3-(1-methyl-1H-tetrazol-5-ylthiomethyl)-1-oxadethia-3-cephem-4-carboxylic acid (54 mg) as a powder. Yield: 79%.

mp. 173°–176° C. (d)

IR $\nu_{max}^{KBr}$: 3295, 1783, 1740, 1710, 1682 cm$^{-1}$.

EXAMPLE 23

To a solution of 7α-methoxy-7β-[D-α-phenyl-N-(4-ethyl-2,3-dioxo-1-piperazinylcarbonyl)glycylamino]3-(1-methyl-1H-tetrazol-5-ylthiomethyl)-1-oxadethia-3-cephem-4-carboxylic acid (2 g) in ethyl acetate (40 ml) is added a solution of sodium acetate (0.4 g) in methanol (4.35 ml). The mixture is stirred for 15 minutes, then kept at 0° C. for 1 hour and filtered. The precipitate obtained by filtration is washed with a mixture of methanol and ethyl acetate (1:2), ethyl acetate and ether, successively and dried to give the sodium salt of the starting compound (1.9 g). Yield: 95%.

IR $\nu_{max}^{KB}$: 3200-2700, 1665 cm$^{-1}$.

EXAMPLE 24

(1) Sodium salt of 7α-methoxy-7β-[D-α-phenyl-N-(4-ethyl-2,3-dioxo-1-piperazinylcarbonyl)glycylamino]-3-(1-methyl-1H-tetrazol-5-ylthiomethyl)-1-oxadethia-3-cephem-4-carboxylic acid (0.2 g) in a 5 ml vial is dissolved in 1 ml of water for intravenous injection and infused to an adult patient suffering from urinary tract infection caused by *Klebsiella pneumoniae.*

(2) Powder of 7-[D-α-(p-hydroxyphenyl)-N-(4-ethyl-2,3-dioxo-1-piperazinylcarbonyl)glycylamino]-3-(1-methyl-1H-tetrazol-5-ylthiomethyl)-1-oxadethia-3-cephem-4-carboxylic acid (100 mg) is mixed with corn starch (150 mg), magnesium stearate (10 mg), and talc (10 mg), and the mixed powder is encapsulated in a hard gelatin capsule (250 mg volume). Each one capsule is administered 4 times a day to a patient suffering from upper respiratory tract infection caused by *Staphylococcus aureas.*

(3) Microcrystals of sodium 7-[D-α-phenyl-N-(N-methyl-N-cinnamoylcarbamoyl)glycylamino]-3-(1-methyl-1H-tetrazol-5-yl-thiomethyl)-1-oxadethia-3-cephem-4-carboxylate (0.1 g) and sodium hydrogen phosphate placed in a vial is dissolved in sterilized water for injection (4 ml) and infused to a post operative patient for prevention of bacterial infection.

What we claim is:

1. A compound of the following formula or its pharmaceutically acceptable salt:

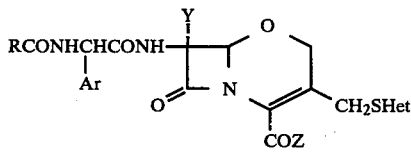

wherein

R is 1,3-dimethylureido, 1,3-dimethylthioureido, 3-methanesulfonyl-2-oxoimidazolidin-1-yl, N-methyl-N-cinnamoylamino, 3,4-di-acetoxyphenyl, 4-oxothiopyran-3-yl, 8-ethyl-3-methoxy-5-oxo-5,8-dihydropyrido[2,3-c]pyridazin-6-yl, 4-methyl-2,3-dioxopiperazin-1-yl, 4-ethyl-2,3-dioxopiperazin-1-yl, or 4-propyl-2,3-dioxopiperazin-1-yl;

Ar is phenyl, hydroxyphenyl, carbamoyloxyphenyl, hydroxyfluorophenyl, or acetoxyphenyl;

Y is hydrogen or methoxy; and

Het is 1-methyltetrazol-5-yl, 1,3,4-thiadiazol-5-yl, 2-methyl-1,3,4-thiadiazol-5-yl, or 1,2,3-thiazol-4-yl.

2. A compound claimed in claim 1, wherein Y is hydrogen, Ar is phenyl or p-hydroxyphenyl, Het is 1-methyltetrazol-5-yl, and R is 1,3-dimethylureido.

3. A compound claimed in claim 1, wherein Y is hydrogen, Ar is phenyl or p-hydroxyphenyl, Het is 1-methyltetrazol-5-yl, and R is 1,3-dimethylthioureido.

4. A compound claimed in claim 1, wherein Y is hydrogen, Ar is phenyl or p-hydroxyphenyl, Het is 1-methyltetrazol-5-yl, and R is 3-methanesulfonyl-2-oxoimidazolidin-1-yl.

5. A compound claimed in claim 1, wherein Y is hydrogen, Ar is phenyl, Het is 1-methyltetrazol-5-yl, and R is N-methyl-N-cinnamoylamino.

6. A compound claimed in claim 1, wherein Y is hydrogen, Ar is phenyl, Het is 1-methyltetrazol-5-yl, and R is 3,4-diacetoxyphenyl.

7. A compound claimed in claim 1, wherein Y is hydrogen, Ar is phenyl, Het is 1-methyltetrazol-5-yl, and R is 8-ethyl-3-methoxy-5-oxo-5,8-dihydropyrido[2,3-c]pyridazin-6-yl.

8. A compound claimed in claim 1, wherein Y is methoxy, Ar is phenyl, Het is 1-methyltetrazol-5-yl, and R is 4-propyl-2,3-dioxopiperazin-1-yl.

9. A compound claimed in claim 1, wherein Y is methoxy, Ar is p-hydroxyphenyl, Het is 1-methyltetrazol-5-yl, and R is 4-propyl-2,3-dioxopiperazin-1-yl.

10. A compound claimed in claim 1, wherein Y is methoxy, Ar is p-hydroxyphenyl, Het is 2-methyl-1,3,4-thiadiazol-5-yl, and R is 4-propyl-2,3-dioxopiperazin-1-yl.

11. A compound claimed in claim 1, of the following formula or a pharmaceutically acceptable salt thereof:

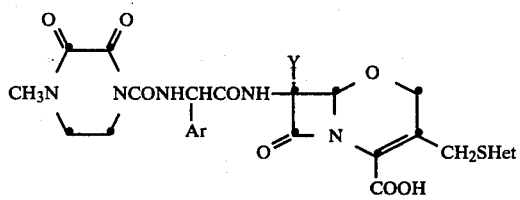

wherein (1) Y is hydrogen, Ar is phenyl, and Het is 1-methyltetrazol-5-yl;

(2) Y is hydrogen, Ar is phenyl, and Het is 2-methyl-1,3,4-thiadiazol-5-yl;

(3) Y is hydrogen, Ar is phenyl, and Het is 1,3,4-thiadiazol-5-yl;

(4) Y is hydrogen, Ar is p-hydroxyphenyl, and Het is 1-methyltetrazol-5-yl;

(5) Y is hydrogen, Ar is p-hydroxyphenyl, and Het is 2-methyl-1,3,4-thiadiazol-5-yl;

(6) Y is hydrogen, Ar is p-hydroxyphenyl, and Het is 1,3,4-thiadiazol-5-yl;

(7) Y is hydrogen, Ar is p-carbamoyloxyphenyl, and Het is 1-methyltetrazol-5-yl;

(8) Y is hydrogen, Ar is p-carbamoyloxyphenyl, and Het is 2-methyl-1,3,4-thiadiazol-5-yl;

(9) Y is hydrogen, Ar is p-carbamoyloxyphenyl, and Het is 1,3,4-thiadiazol-5-yl;

(10) Y is hydrogen, Ar is p-acetoxyphenyl, and Het is 1-methyltetrazol-5-yl;

(11) Y is methoxy, Ar is phenyl, and Het is 1-methyltetrazol-5-yl;

(12) Y is methoxy, Ar is phenyl, and Het is 2-methyl-1,3,4-thiadiazol-5-yl;

(13) Y is methoxy, Ar is phenyl, and Het is 1,3,4-thiadiazol-5-yl;

(14) Y is methoxy, Ar is p-hydroxyphenyl, and Het is 1-methyltetrazol-5-yl;

(15) Y is methoxy, Ar is p-hydroxyphenyl, and Het is 2-methyl-1,3,4-thiadiazol-5-yl;

(16) Y is methoxy, Ar is p-hydroxyphenyl, and Het is 1,3,4-thiadiazol-5-yl;

(17) Y is methoxy, Ar is p-carbamoyloxyphenyl, and Het is 1-methyltetrazol-5-yl;

(18) Y is methoxy, Ar is p-carbamoyloxyphenyl, and Het is 2-methyl-1,3,4-thiadiazol-5-yl;

(19) Y is methoxy, Ar is p-carbamoyloxyphenyl, and Het is 1,3,4-thiadiazol-5-yl; or

(20) Y is methoxy, Ar is 4-hydroxy-2-fluorophenyl, and Het is 1,2,3-triazol-4-yl.

12. A compound claimed in claim 1, of the following formula or a pharmaceutically acceptable salt thereof:

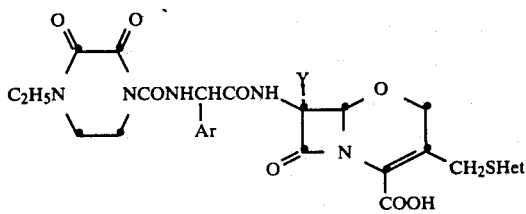

wherein
(1) Y is hydrogen, Ar is phenyl, and Het is 1-methyltetrazol-5-yl;
(2) Y is hydrogen, Ar is phenyl, and Het is 2-methyl-1,3,4-thiadiazol-5-yl;
(3) Y is hydrogen, Ar is phenyl, and Het is 1,3,4-thiadiazol-5-yl;
(4) Y is hydrogen, Ar is p-hydroxyphenyl, and Het is 1-methyltetrazol-5-yl;
(5) Y is hydroen, Ar is p-hydroxyphenyl, and Het is 2-methyl-1,3,4-thiadiazol-5-yl;
(6) Y is hydrogen, Ar is p-hydroxyphenyl, and Het is 1,3,4-thiadiazol-5-yl;
(7) Y is hydrogen, Ar is p-carbamoyloxyphenyl, and Het is 1-methyltetrazol-5-yl;
(8) Y is hydrogen, Ar is p-carbamoyloxyphenyl, and Het is 2-methyl-1,3,4-thiadiazol-5-yl;
(9) Y is hydrogen, Ar is p-carbamoyloxyphenyl, and Het is 1,3,4-thiadiazol-5-yl;
(10) Y is hydrogen, Ar is p-acetoxyphenyl, and Het is 1-methyltetrazol-5-yl;
(11) Y is methoxy, Ar is phenyl, and Het is 1-methyltetrazol-5-yl;
(12) Y is methoxy, Ar is phenyl, and Het is 2-methyl-1,3,4-thiadiazol-5-yl;
(13) Y is methoxy, Ar is phenyl, and Het is 1,3,4-thiadiazol-5-yl;
(14) Y is methoxy, Ar is p-hydroxyphenyl, and Het is 1-methyltetrazol-5-yl;
(15) Y is methoxy, Ar is p-hydroxyphenyl, and Het is 2-methyl-1,3,4-thiadiazol-5-yl;
(16) Y is methoxy, Ar is p-hydroxyphenyl, and Het is 1,3,4-thiadiazol-5-yl;
(17) Y is methoxy, Ar is p-carbamoyloxyphenyl, and Het is 1-methyltetrazol-5-yl;
(18) Y is methoxy, Ar is p-carbamoyloxyphenyl, and Het is 2-methyl-1,3,4-thiadiazol-5-yl;
(19) Y is methoxy, Ar is p-carbamoyloxyphenyl, and Het is 1,3,4-thiadiazol-5-yl; or
(20) Y is methoxy, Ar is 4-hydroxy-2-fluorophenyl, and Het is 1,2,3-triazol-4-yl.

13. A compound claimed in claim 1, wherein the pharmaceutically acceptable salt is a sodium or potassium salt.

14. The compound claimed in claim 12, namely 7α-methoxy-7β-[D-α-phenyl-N-(4-ethyl-2,3-dioxo-1-piperazinylcarbonyl)glycylamino]-3-(1-methyl-1H-tetrazol-5-ylthiomethyl)-1-oxadethia-3-cephem-4-carboxylic acid.

15. An antibacterially active pharmaceutical composition which comprises an antibacterially effective amount of a compound according to claim 1 or pharmaceutically acceptable salt thereof and a pharmaceutically acceptable carrier therefor.

16. A method for the treatment of a human or veterinary bacterial infection which comprises administering to a patient or animal suffering from said bacterial infection an antibacterially effective amount of a compound according to claim 1 or a pharmaceutically acceptable salt thereof.

* * * * *